US012586206B2

(12) United States Patent
Sabczynski et al.

(10) Patent No.: US 12,586,206 B2
(45) Date of Patent: Mar. 24, 2026

(54) METHOD FOR IDENTIFYING A MATERIAL BOUNDARY IN VOLUMETRIC IMAGE DATA

(71) Applicant: KONINKLIJKE PHILIPS N.V., Eindhoven (NL)

(72) Inventors: Jörg Sabczynski, Norderstedt (DE); Rafael Wiemker, Kisdorf (DE); Tobias Klinder, Uelzen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 325 days.

(21) Appl. No.: 18/266,030

(22) PCT Filed: Dec. 7, 2021

(86) PCT No.: PCT/EP2021/084510
§ 371 (c)(1),
(2) Date: Jun. 8, 2023

(87) PCT Pub. No.: WO2022/122698
PCT Pub. Date: Jun. 16, 2022

(65) Prior Publication Data
US 2024/0037754 A1     Feb. 1, 2024

(30) Foreign Application Priority Data
Dec. 9, 2020     (EP) ..................................... 20212738

(51) Int. Cl.
*G06K 9/00*          (2022.01)
*A61B 6/00*          (2006.01)
(Continued)

(52) U.S. Cl.
CPC ............. *G06T 7/13* (2017.01); *A61B 6/5205* (2013.01); *G06T 7/0012* (2013.01); *G06T 17/20* (2013.01);
(Continued)

(58) Field of Classification Search
CPC .. G06K 9/00; G06F 18/41; G06T 5/30; G06T 7/13
(Continued)

(56) References Cited

U.S. PATENT DOCUMENTS 5,920,319 A     7/1999 Vining
9,153,033 B2   10/2015 Takeguchi
(Continued)

FOREIGN PATENT DOCUMENTS

WO     WO0022573 A1     4/2000
WO     WO0229723 A1     4/2002

OTHER PUBLICATIONS

PCT International Search Report, International application No. PCT/EP2021/084510, Jun. 7, 2022.
(Continued)

*Primary Examiner* — Seyed H Azarian
(74) *Attorney, Agent, or Firm* — Larry Liberchuk

(57)          ABSTRACT

A method for identifying a material boundary within volumetric image data is based on use of a model boundary transition function, which models the expected progression of voxel values across the material boundary, as a function of distance. Each voxel is taken in turn, and voxel values within a subregion surrounding the voxel are fitted to the model function, and the corresponding fitting parameters are derived, in addition to a parameter relating to quality of the model fit. Based on these parameters for each voxel, for each of at least a subset of the voxels, a candidate spatial point is identified, estimated to lie on the material boundary within the 3-D image dataset. The result is a cloud of candidate spatial points which spatially correspond to the outline of the boundary wall. Based on these, a representation of the boundary wall can be generated, for example a surface mesh.

12 Claims, 5 Drawing Sheets

(51) Int. Cl.

| | |
|---|---|
| *G06T 5/30* | (2006.01) |
| *G06T 7/00* | (2017.01) |
| *G06T 7/13* | (2017.01) |
| *G06T 17/20* | (2006.01) |
| *G16H 30/40* | (2018.01) |

(52) U.S. Cl.
CPC ... *G16H 30/40* (2018.01); *G06T 2207/10081* (2013.01); *G06T 2207/30028* (2013.01); *G06T 2210/41* (2013.01); *G06T 2210/56* (2013.01)

(58) Field of Classification Search
USPC ....... 382/100, 103, 106, 128–133, 154, 156, 382/162, 168, 173, 181, 199, 219, 224, 382/254, 285–291, 305, 321; 345/424; 378/4, 21
See application file for complete search history.

(56) References Cited

U.S. PATENT DOCUMENTS

| | | | | |
|---|---|---|---|---|
| 2007/0053553 | A1 | 3/2007 | Gerritsen | |
| 2008/0273781 | A1* | 11/2008 | Manduca | G06T 5/30 |
| | | | | 382/131 |
| 2009/0238404 | A1* | 9/2009 | Orderud | G06T 7/149 |
| | | | | 382/103 |
| 2012/0320055 | A1* | 12/2012 | Pekar | G06T 7/143 |
| | | | | 345/424 |
| 2014/0122112 | A1* | 5/2014 | Bzdusek | G06T 7/30 |
| | | | | 382/128 |
| 2018/0137626 | A1* | 5/2018 | Lawrenson | G06F 18/41 |
| 2018/0308278 | A1* | 10/2018 | Qiu | G06T 15/005 |

OTHER PUBLICATIONS

Serlie I. et al., "Computed Cleansing for Virtual Colonoscopy Using a Three-Material Transition Model", Lecture Notes in Computer Science—Medical Image Computing and Computer-Assisted Intervention, MICCAI 2003—6th International Conference Proceedings—Nov. 15-18, 2003, Montreal, Canada, Nov. 15, 2003 (Nov. 15, 2003), Springer Berlin Heidelberg, Berlin, Heidelberg, XP055096939.

Babaheidarian P. et al., "Joint Reconstruction and Material Classification in Spectral CT", Proceedings of SPIE; [Proceedings of SPIE ISSN 0277-786X vol. 10524], SPIE, US, vol. 10632, Apr. 27, 2018 (Apr. 27, 2018), pp. 106320D-106320D, XP060106146.

Lorensen W.E. et al., "Marching Cubes: A High Resolution 3d Surface Construction Algorithm", ACM SIGGRAPH Computer Graphics, Aug. 1987.

* cited by examiner

10

METHOD FOR IDENTIFYING A MATERIAL BOUNDARY IN VOLUMETRIC IMAGE DATA

FIELD OF THE INVENTION

The present invention relates to an image processing method, in particular for identifying a material boundary in volumetric image data.

BACKGROUND OF THE INVENTION

In the field of volumetric imaging, it is commonly useful to be able to identify and visualize a boundary or wall of a particular structure within the imaged region. This need arises for example in the field of medical imaging, where it is useful to generate a representation of the morphology of a wall of a particular anatomical structure, such as an organ or portion thereof. One particular field where this is useful is the field of virtual colonoscopy.

Virtual Colonoscopy is the visual inspection of the colon wall using volumetric image data, for example acquired using x-ray computed tomography (CT) imaging. Visualizing the colon wall is typically done using Volume Rendering techniques, resulting in an image impression similar to the view of a real endoscope during colonoscopy.

Colonoscopy can be used to identify polyps in the colon. Polyps in the colon can possibly develop into colon cancer. If removed early, cancer can be prevented effectively. It is therefore recommended, even for asymptomatic patients above a certain age, to perform endoscopic inspection of the colon (colonoscopy) in order to detect and assess possible polyps. Unfortunately, compliance with this screening is low, mainly due to the discomfort associated with endoscopy.

Therefore, non-invasive virtual colonoscopy (VC), based on CT scanning, has been developed as an alternative.

VC typically uses direct volume rendering techniques. In direct volume rendering, a transfer function (TF) is used which maps for each voxel of a CT volumetric image dataset its Hounsfield density value to an opacity and color value. This opacity and color is then projected into the VC image to create a virtual rendering of the colon.

This approach has several disadvantages.

First, depending on the form and parameters of the transfer function, the apparent position of the colon wall in the rendered image may differ and may not accurately coincide with the real colon wall position.

A second problem can arise due to the presence of residual stool or faeces within the colon. This has a contrast within CT scan data which is similar to the colon wall tissue. Its presence can therefore obscure view of the colon wall. To overcome this, typically a process called Virtual Cleansing is performed. This usually comprises a preprocessing step in which portions of the image relating to residual stool or faeces is removed. This pre-processing of the image is usually supported by orally administering a laxative to remove stool followed by administering a contrast agent containing iodine prior to CT imaging in order to tag remaining stool. This tagging assists in digitally removing the remaining faeces from the image after data acquisition.

However, voxel-wise Virtual Cleansing (VC) methods rely on knowing the Hounsfield values of pure materials. Usually it is assumed that there are three different classes of relevant materials in VC: air, soft tissue, and tagged faeces. However, with the exception of air, the Hounsfield values of soft tissue and tagged faeces vary, not only from CT image to CT image, but also within a single CT image. Therefore, cleansing methods relying on the knowledge of the Hounsfield values of pure materials can produce artefacts in the rendered images. Furthermore, even when the material properties of the pure materials are known exactly, voxel-wise rendering methods can produce geometric artefacts at the three-material transitions. In VC, these appear as "water level" artefacts at the colon wall, where all three pure materials (air, tissue, tagged faeces) meet.

An improved approach to identifying material boundaries within a volumetric imaging dataset would be of value, not only for virtual colonoscopy, but for imaging of any region in which boundaries of a target object of interest are to be identified.

SUMMARY OF THE INVENTION

The invention is defined by the claims.

According to examples in accordance with an aspect of the invention, there is provided a method of processing volumetric image data for identifying a material boundary within the data, the method comprising:

obtaining volumetric image data representative of anatomical region of a subject;

for each of at least a subset of voxels in the anatomical region:

identifying a volumetric sub-region surrounding the voxel, the sub-region including at least a subset of directly neighboring voxels;

retrieving a pre-determined boundary transition function, the boundary transition function representing a model of expected voxel values as a function of distance across the material boundary to be identified;

fitting the pre-determined boundary transition function to the voxel values comprised within the volumetric sub-region, the fitting comprising determining fitting parameters of the model function;

determining a fit quality parameter indicative of a quality of the model function fit;

identifying candidate spatial points for the location of the material boundary based on the determined fitting parameters and fit quality parameter for each voxel;

estimating the material boundary within the data based on at least a subset the identified candidate points.

Embodiments of the present invention are based on a different approach to deriving a representation of a material boundary wall, based on models of material transitions. In the proposed approach, a prior-generated model function is used which models the progression of voxel values across a material boundary. Based on fitting a region surrounding each voxel to this model, and calculating the fitting parameters and a quality of the fit, a candidate spatial point can be identified for each of at least a subset of the voxels, estimated to lie on or near the boundary.

For some examples, an additional step can be performed wherein, based on the fitting parameters and a quality of the fit for each voxel, the particular subset of voxels which are most likely to lie on the material boundary can be first identified as candidate voxels. A respective boundary spatial point can then be identified for each of these candidate voxels. These may then be further filtered down based on model fit parameters, e.g. for the distance of each of the voxels to the material boundary.

This is hence a completely different approach to identifying a material boundary wall compared for example to the more typical volume rendering techniques. As discussed above, volume rendering uses a transfer function (TF) to map each and every voxel from a respective voxel density value to an opacity and color value. The approach according to embodiments of the present invention is tailored specifically to identifying a material boundary and aims to identify spatial points which correspond to the location of the material boundary based on the results of fitting a prior-determined material transition function to a volumetric region surrounding each voxel. The spatial points are inter-voxel spatial points, i.e. can lie between the co-ordinate positions marking the center of each voxel.

This approach provides more accurate results for the rendered boundary wall, both in terms of position and shape, and reduces geometric artefacts which can arise using volume rendering techniques.

This approach can be advantageously used within the field of virtual colonoscopy imaging, but also within a wide range of other fields, both medical imaging fields, and outside of the medical imaging domain. The approach can be used for volumetric image data representative of any region which contains material boundaries, the locations of which are desired to be identified.

Preferably, the volumetric sub-region surrounding each voxel includes all directly neighboring voxels.

Identifying the candidate spatial points may be based on further (secondary) parameters derived from the fitting parameters and/or the quality fit parameter.

The boundary transition function may model the voxel values as progressing from a minimum voxel value, $m_{low}$, on one side of the material boundary to a maximum voxel value, $m_{high}$, on the other side of the material boundary.

The fitting parameters include one or more of:
the minimum voxel value, $m_{low}$;
the maximum voxel value, $m_{high}$;
a perpendicular distance, d, of the voxel from the material boundary;
a unit normal vector of the material boundary.

Perpendicular distance means a distance along a direction normal to the boundary.

The fitting parameters may further include the width, σ, of the point spread function of the data acquisition equipment (e.g. the CT scanner).

Some of the fitting parameters may be known in advance (e.g. σ), and some may be determined.

The identifying of the candidate spatial points may be based on the determined values of the one or more fitting parameters, and/or based on further parameters derived from the fitting parameters. The further derived parameters may include for example absolute difference between $m_{high}(i)$ and $m_{low}(i)$ and/or a parameter indicative of a gradient of at least a portion of the function.

The fit quality parameter is a quantity characterizing the fitting quality of the model function fit. In examples, the fit quality parameter may include any one or more of: a measure of a fit optimality criterion, goodness of fit, a residual from the fitting, a measure of fitting success, and tolerance of the result.

The identifying of the candidate spatial points may in some embodiments comprise a preliminary step of identifying candidate voxels, and wherein a respective candidate point is identified based on the fitting parameters for each candidate voxel. In other words, this is a step of reducing or filtering the total set of voxels down to those most likely to yield an estimated boundary spatial point which is accurate or reliable. The identifying of the candidate voxels may be based on the determined fitting parameters and/or fit quality parameter for each voxel.

The identifying of the candidate voxels may be based on reference values for the various parameters derived for each voxel (model fitting parameters, quality fit parameter, or any quantities derived from these). The reference values may correspond to expected values of these parameters for a particular material boundary of interest. For example, the typical $m_{high}$ and $m_{low}$ on either side of a target material boundary may be known in advance, for example through data from previous scans of a region containing the boundary. Thus, candidate voxels can be identified as those for which the derived parameter values are within a predefined tolerance range of the reference values.

Identifying the candidate voxels may in some examples be based on further (secondary) parameters derived from the fitting parameters and/or the quality fit parameter.

In some examples, the identifying of the candidate voxels may comprise performing masking of voxels in the imaged anatomical region, based on one or more of the derived fitting parameter values and/or based on the derived quality parameter values.

A separate respective mask may be generated for each of the different fitting parameters and for the quality fit parameter. A plurality of these may be applied in combination to the volumetric image data in some examples, and the resulting voxels located in the mutually overlapping regions of the set of masks may be identified as the candidate voxels.

In some examples, new images or image representations of the imaged anatomical region may be generated based on each of the derived fitting parameters and quality fit parameters, and any secondary parameters derived therefrom. In particular, a new respective image representation of the imaged region may be derived for each parameter, with voxel values for each voxel set equal to the respective derived parameter value for that voxel.

Masking may then be applied to each of the new constructed images, based on reference values for the corresponding parameter that the constructed image represents. In some examples, these masks may be combined into a single mask and applied to the original volumetric image data to identify the candidate voxels as those located in areas of overlap between all of the masks.

In some examples, the criteria used in the masking are configured to identify voxels for which the material boundary is located within the volumetric sub-region of the voxel. However, this is not essential.

A separate respective mask may be generated/applied based on each of one or more of:
the quality fit parameter for each voxel, wherein each voxel is masked in dependence upon the quality fit parameter exceeding a pre-defined reference value for the quality fit;
the values of $m_{high}$ and $m_{low}$ for each voxel, wherein each voxel is masked in dependence upon the derived values of $m_{high}$ and $m_{low}$ falling within a pre-defined tolerance range of a pre-determined pair of reference values for $m_{high}$ and $m_{low}$, the reference values corresponding to a particular material boundary of interest; and
the distance, d, for each voxel, wherein each voxel is masked in dependence upon the derived distance value, d, falling within a pre-defined tolerance range of a reference value for d.

In advantageous examples, the masking is done at least for the quality fit parameter and the values of $m_{high}$ and $m_{low}$, since these most directly reflect the correspondence of the voxel to a voxel region which is close to the material boundary of interest. A separate mask may be generated for each of $m_{high}$ and $m_{low}$, or a single mask may be generated for the combined pair of values.

In accordance with one or more embodiments, a plurality of masks may be generated for different respective parameters and applied in combination to the volumetric image data, and wherein the resulting voxels located in mutually overlapping regions of the combination of masks are identified as the candidate voxels.

Candidate spatial points may then be derived for each of the candidate voxels. The resulting set of candidate spatial points derived from the candidate voxels typically represents a cloud of candidate points for the material boundary, the cloud delimiting the material boundary to be identified.

As an alternative to first identifying a set of candidate voxels, and then determining the candidate spatial points from each the candidate voxels, instead the process can be done voxel-by-voxel, wherein each voxel is assessed in turn to determine whether it meets the pre-defined criteria to be a candidate voxel and, if so, a candidate spatial point is determined using the fitting parameters derived for that voxel. In this alternative example, no separate masking step is needed. The same assessment criteria discussed above for deriving the masks can instead be applied voxel-by-voxel.

In some examples, the fitting parameters for each voxel may include a perpendicular distance, d, of the voxel from the material boundary, and a unit normal vector of the material boundary. The identifying the candidate spatial point for the voxel may then comprises identifying co-ordinates of a point a distance d from the voxel position along the unit normal direction.

In accordance with one or more embodiments, the deriving the estimating the material boundary further comprises generating a surface mesh representative of the material boundary, the surface mesh containing at least a subset of the identified candidate spatial points.

The deriving the mesh may comprise linking spatial points from the at least subset of spatial points into triangles.

This provides for a clearer rendering of the surface.

However, the deriving of the mesh is not essential, and instead a different representation of the material boundary may be generated. For example simply an array of the spatial point coordinate positions which have been identified as corresponding to the location of the material boundary may be used as the representation.

In accordance with one or more embodiments, the obtained volumetric image data may be x-ray CT volumetric image data.

In some examples, the method may comprise receiving CT projection data, and performing an image reconstruction to thereby obtain the volumetric image data. In other examples, the method may comprise receiving already reconstructed volumetric image data.

Alternatives to CT data include for example MRI image data or volumetric ultrasound data.

In accordance with one or more embodiments, the obtained volumetric image data may be spectral image data. The data may include a plurality of image data sets, each formed from data corresponding to a different spectral data channel, and wherein the method according to the invention is performed for each of the data sets, and wherein there is a different respective pre-determined material transition function for each spectral channel.

One example is the use of x-ray spectral CT data. X-ray spectral CT is an imaging modality that extends the capabilities of a conventional x-ray CT system by acquiring projection data for a plurality of x-ray energies. This can be done by incorporating a detector which can discriminate between different x-Ray energies, e.g. an energy discriminating photon counting detector or energy integrating detector, or by sequentially changing the x-ray energy spectrum and sequentially acquiring corresponding detector data. Spectral x-ray data allows for discerning and quantifying materials comprised by the scanned object. This is because different materials may have different x-ray absorption spectra. An x-ray energy spectrum can be used which is known to be maximally or minimally absorbed by a material of interest for example.

By generating different material boundary representations using data from different spectral channels, this can provide supplementary information since image data from different spectral channels will vary depending upon material composition of the imaged object. For example, boundaries between multiple pairs of different materials can be identified and combined to enhance the identification of boundary wall of an organ which may be marked by different material transitions.

By way of one example, spectral-CT imaging can be used in the field of CT colonography to generate a number of spectral channels (at least two) corresponding to the lower and high-energy levels of the projected x-ray energy. The spectral channels can be converted into various representations, including for example iodine-density maps, which can enable visualization of contrast agent distribution within the imaged colon. In the context of colonography, the multiple spectral channel data can be used in some embodiments to assist in performing the virtual cleansing (as discussed above).

In accordance with one or more embodiments, the material boundary to be identified may represent a structural wall of an anatomical structure.

In some examples, the material boundary to be identified may represent a wall of an anatomical structure delimiting an interior lumen, e.g. a colon.

Examples in accordance with a further aspect of the invention provide a computer program product comprising computer program code, the computer program code being executable on a processor to cause the processor to perform a method in accordance with any example or embodiment outlined above or described below, or in accordance with any claim of this application.

Examples in accordance with a further aspect of the invention also provide a processing arrangement for processing volumetric image data for identifying a material boundary within the data. The processing arrangement is adapted to:

obtain volumetric image data representative of anatomical region of a subject;

for each voxel in the anatomical region:

identify a volumetric sub-region surrounding the voxel, the sub-region including at least a subset of directly neighboring voxels;

retrieve a pre-determined boundary transition function, the boundary transition function representing a model of expected voxel values as a function of distance across the material boundary to be identified;

fit the pre-determined boundary transition function to the voxel values comprised within the volumetric sub-region, the fitting comprising determining fitting parameters of the model;

determine a fit quality parameter indicative of a quality of the model function fit;

identify candidate spatial points for the material boundary based on the determined fitting parameters and fit quality parameter for each voxel; and estimate the material boundary within the data based on at least a subset the identified candidate points.

In accordance with one or more embodiments, the boundary transition function may model the voxel values as progressing from a minimum voxel value, $m_{low}$, on one side of the material boundary to a maximum voxel value, $m_{high}$, on the other side of the material boundary, and wherein the fitting parameters include one or more of:

the minimum voxel value, $m_{low}$;

the maximum voxel value, $m_{high}$;

a perpendicular distance, d, of the voxel from the boundary;

a unit normal vector of the boundary.

In some examples, the identifying of the candidate spatial points may comprise a preliminary step of identifying candidate voxels, and wherein a respective candidate point is identified based on the fitting parameters for each candidate voxel. The identifying of candidate voxels may comprise performing masking of voxels in the imaged anatomical region, based on one or more of the derived fitting parameter values and/or based on the derived fit quality parameter values.

In some examples, a separate respective mask may be applied based on each of one or more of:

the quality fit parameter for each voxel, wherein each voxel is masked in dependence upon the quality fit parameter exceeding a pre-defined reference value for the quality fit;

the values of $m_{high}$ and $m_{low}$ for each voxel, wherein each voxel is masked in dependence upon the derived values of $m_{high}$ and $m_{low}$ falling within a pre-defined tolerance range of a pre-determined pair of reference values for $m_{high}$ and $m_{low}$, the reference values corresponding to a particular material boundary of interest;

the distance, d, for each voxel, wherein each voxel is masked in dependence upon the derived distance value, d, falling within a pre-defined tolerance range of a reference value for d.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
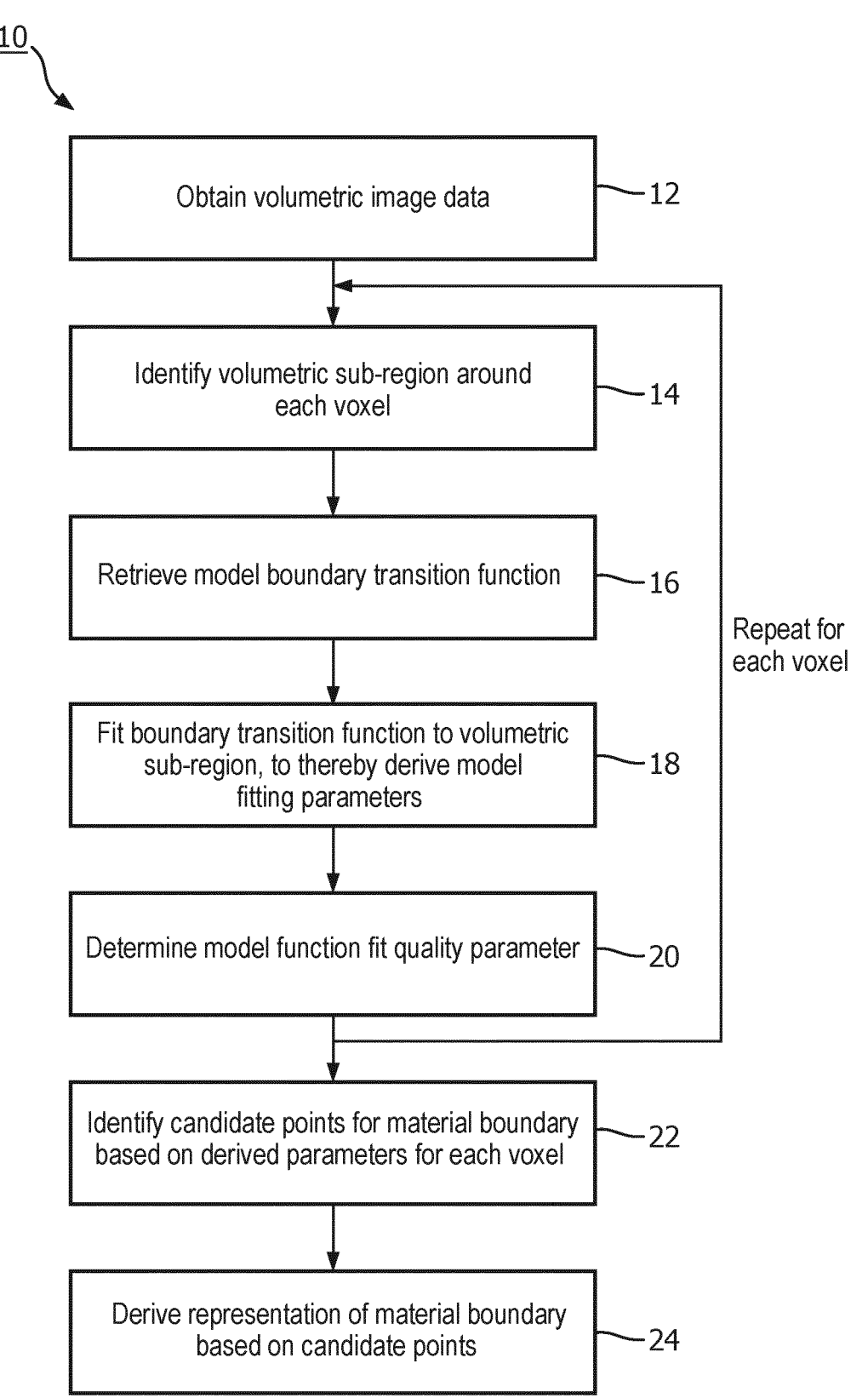
FIG. 1 outlines steps of an example method according to one or more embodiments.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a new approach to identifying a material boundary within volumetric image data. The approach is based on use of a model boundary transition function which models the expected progression of voxel values across the material boundary as a function of distance. Each voxel is taken in turn, and voxel values within a subregion surrounding the voxel are fitted to the model function, and the corresponding fitting parameters are derived, in addition to a parameter relating to quality of the model fit. Based on these parameters for each voxel, for each of at least a subset of the voxels, a candidate spatial point is identified, estimated to lie on the material boundary within the 3-D image dataset. Additional preliminary steps may optionally be applied to filter the voxels down to candidate voxels, for example based on an estimated distance of each voxel to the material boundary, where this can be estimated based on a particular combination of the derived model parameters for each voxel. Candidate points can be identified just for the identified candidate voxels. The result is a cloud of candidate spatial points which spatially correspond to the outline of the boundary wall. Based on these, a representation of the boundary wall can be generated, for example a surface mesh.

FIG. 1 shows a block diagram outlining the basic steps of an example method according to one or more embodiments. The method 10 is a computer implemented method. The method is for processing volumetric image data for identifying a material boundary within the data.

The method 10 comprises obtaining 12 volumetric image data representative of anatomical region of a subject.

The method 10 further comprises, for each of at least a subset of voxels in the anatomical region, performing each of the following steps:

identifying 14 a volumetric sub-region surrounding the voxel, the sub-region including at least a subset of directly neighboring voxels;

retrieving 16 a pre-determined boundary transition function, representative of a pre-determined model function of voxel values with respect to distance across the material boundary to be identified;

fitting 18 the pre-determined boundary transition function to the voxel values comprised within the volumetric sub-region, the fitting comprising determining fitting parameters of the model function; and determining 20 a fit quality parameter indicative of a quality of the model function fit.

In some examples, the above steps are performed for every voxel in the imaged region. However, in other examples, one or more pre-processing steps may be performed for removing or filtering certain voxels (estimated to be unlikely candidates for coinciding with the boundary position) before the main method is applied.

Once the above has been done for each relevant voxel, the method further comprises a process 22 of identifying candidate spatial points for the boundary wall based on the determined fitting parameters and the fit quality parameter for each voxel. For example, in one set of embodiments, the fitting parameters may include a perpendicular distance, d, of the voxel from the material boundary, and a unit normal vector of the material boundary, and determining the candidate spatial point comprises determining co-ordinates of a point a distance d from the voxel position along the unit normal direction.

Once the candidate spatial points have been identified 22, the method further comprises estimating 24 the material boundary within the data based on the identified candidate spatial points.

In some examples, a surface mesh may be generated based on the identified candidate spatial points, or based on an extracted subset thereof. In other examples, a representation of the boundary may be generated comprising simply an array of co-ordinate positions of the identified candidate spatial points, or an extracted subset thereof.

The method outlined above may be performed by a processor or a processing arrangement comprising one or more processors. The obtaining of the volumetric image data may comprise receiving the volumetric image data from an external source, such as an imaging apparatus (e.g. a CT or MRI scanning apparatus), or from a datastore. In further examples, the obtaining of the volumetric image data may comprise receiving unreconstructed scan data (e.g. CT projection data), and performing a step of reconstructing the volumetric image data.

Embodiments of the invention are based on mathematical models of the appearance of material transitions between discrete pure material classes in volumetric image data, for example in CT image data. However the same principles can also be applied to other forms of volumetric image data, e.g. MRI.

Depending upon the particular material transition in question, a different model material transition function may be applicable. For example, the different model functions may vary depending upon the tissue densities on each side of the material boundary, the typical distance over which the transition occurs, and potentially geometrical characteristics of the boundary.

Figure 2:
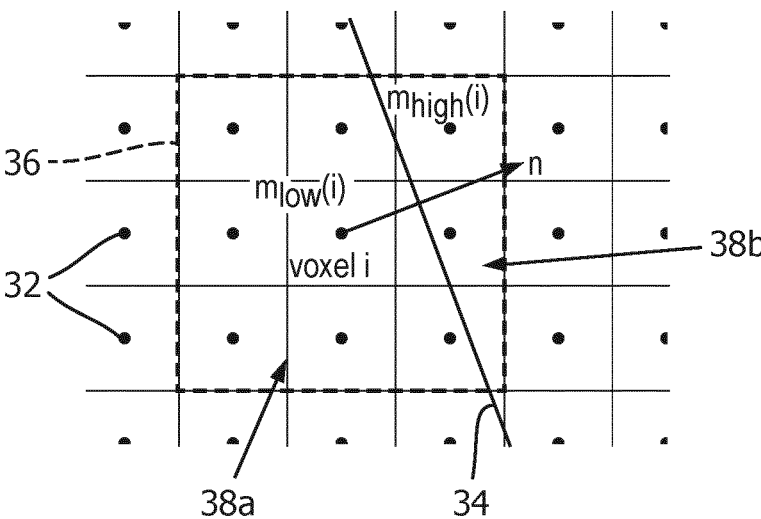
FIG. 2 schematically depicts the modelling parameters used for fitting the model boundary transition function for each voxel according to one or more embodiments.

The model used for the model boundary transition function is schematically illustrated in FIG. 2. This represents a two-material transition. However, the same principles can be applied also for other transitions, e.g. a three-material transition.

With reference to FIG. 2, a two-material transition can be modelled by a model function $g(m_{high}, m_{low}, d, n, \sigma)$ where $m_{low}$ is the expected lower voxel 32 value, and $m_{high}$ is expected higher voxel value of the two pure materials, on a first 38a and second 38b side respectively of the two-material transition boundary 34. By way of example, where the image data is CT image data, the voxel values may be Hounsfield values. The parameter d represents the perpendicular distance from the material boundary 34 to a voxel, i, to which the function is being fitted, and n represents a unit normal vector of the material boundary. The parameter $\sigma$ represents the width of the point spread function of the scanning equipment (e.g. CT scanner).

For each voxel, i, the model function is fitted to voxel 32 values within a volumetric subregion 36 surrounding the voxel. This may be a subregion of fixed size, e.g. extending to one voxel away from the voxel in question on all sides, i.e. a cube of 3 voxels unit length. It may include all directly neighboring voxels. It may include more than directly neighboring voxels, e.g. a cube of 5×5×5 or 7×7×7 voxels or any other number.

Figure 3:
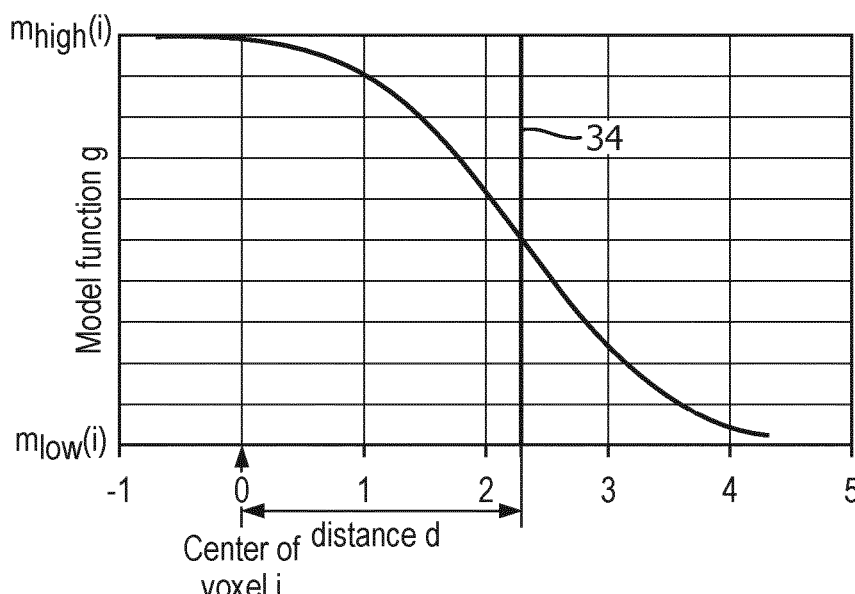
FIG. 3 schematically illustrates an example boundary transition function according to one or more embodiments.

FIG. 3 schematically illustrates an example boundary transition function. The boundary transition function models the voxel 32 values as progressing from a maximum voxel value, $m_{high}$, on one side of the material boundary 34, to a minimum voxel value, $m_{low}$, on the other side of the material boundary 34. The function is non-linear. FIG. 3 depicts a position of an example voxel, i, to which the model might be fitted, and shows the model fitting parameter d, which represents the distance of the voxel from the material boundary 34. In some examples, there may be a pre-defined spatial co-ordinate system for the imaged anatomical region of the subject, and wherein d is represented in units of this co-ordinate system, for example mm. In other examples, it could be represented in units of voxel space (i.e. where a width of one voxel corresponds to a unit length).

One example workflow of the method in accordance with one or more embodiments will now be outlined in detail, from which the general steps of the method will become clearer. The method described here uses a CT image of the abdomen as input. Optionally, any residual faeces may have been tagged with iodine contrast agent prior to imaging.

The method described below is for a two material transition (either air-tissue or air-stool or stool-tissue). However, it may be applied similarly to other transitions, e.g. three-material transitions.

Figure 4:
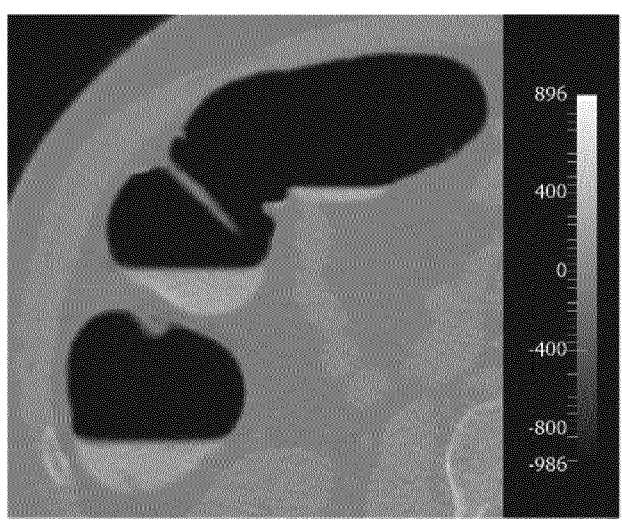
FIG. 4 illustrates one slice through an example volumetric image dataset containing a material boundary to be identified.

The method begins with obtaining the volumetric image data representative of the relevant anatomical region of the subject. FIG. 4 shows one image slice from an example CT volumetric image dataset. In this example, the image dataset is representative of a region containing the colon of a subject.

A particular model boundary transition function, g, specific to a target material boundary is retrieved, for example from a local or remote datastore. In this particular example, the material boundary to be identified corresponds to the wall of the colon. The material boundary may for example be a boundary between the material of stool residue and the colon wall tissue, or a boundary between the air within the lumen of the colon and the colon wall tissue.

Once the model boundary transition function has been retrieved, the model function is fitted to voxel values comprised within a volumetric subregion surrounding each respective voxel in the volumetric image dataset.

This model fit process may be performed for each voxel within the 3-D image dataset in turn (or at least an identified subset of the voxels). For example, the method may iterate or index through the voxels one-by-one, applying the model fitting to each in turn.

For each relevant voxel, i, a volumetric subregion 36 (or local environment) surrounding the voxel is identified, the subregion including at least a subset of directly neighboring voxels. As discussed above, the volumetric subregion could be a cubic subregion of predefined size, e.g. a subregion encompassing every voxel immediately neighboring the voxel i. The subregion may for example be a cubic sub-image of size $k^3$ with voxel i in the center.

The retrieved boundary transition model function, g, is then fitted to the voxel values (e.g. Hounsfield values in this example) located in the sub-region 36. The fitting may for example be done using a least square fit method. However, the skilled person will be aware of a variety of different model fitting methods which may instead be applied. For example, almost any regression method would be suitable, e.g. polynomial regression, logistic regression, multivariate regression.

As a result of the model function fitting, the fitted model parameters (herein: fitting parameters) for each voxel, i, are derived: $m_{high}(i)$, $m_{low}(i)$, $d(i)$, $n(i)$, $\sigma(i)$ (as outlined in more detail above).

In addition, one or more further parameters representative of a quality of the model function fit to the subregion of each voxel, i, can be determined. These depend upon the fitting method used. By way of example, the fit quality parameter (s) may include one or more of: optimality of model fit, residual of a least squares fit, fitting success, tolerance of the fitting result or any other suitable parameter as will be apparent to the skilled person.

Based on the derived fitting parameters, and the fit quality parameter(s) for each voxel, i, further secondary parameters or quantities may be derived. These are not parameters of the model function themselves, but can be calculated from the estimated model parameters. By way of example, these may include: an absolute distance of voxel i from the material transition boundary 24, an absolute difference between $m_{high}(i)$ and $m_{low}(i)$, and/or a gradient or steepness of the model transition function.

In some examples, new respective images or image representations of the imaged anatomical region may be generated representative of each of the derived fitting parameters, quality fit parameters, and any parameters derived therefrom. In particular a new respective image representation of the imaged region may be derived for each parameter, with voxel values for each voxel set equal to the respective derived parameter value for that voxel.

Figure 5:
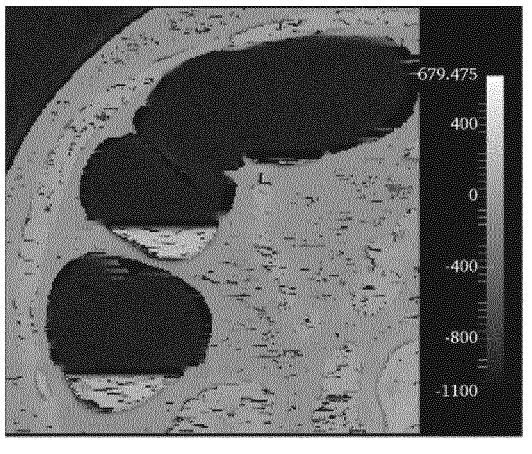
FIG. 5(a) and FIG. 5(b) represent image representations of two model function parameters calculated for each voxel in the image dataset: respectively a minimum voxel value, $m_{low}$, on one side of the material boundary, and maximum voxel value, $m_{high}$, on the other side of the material boundary.
Figure 5:
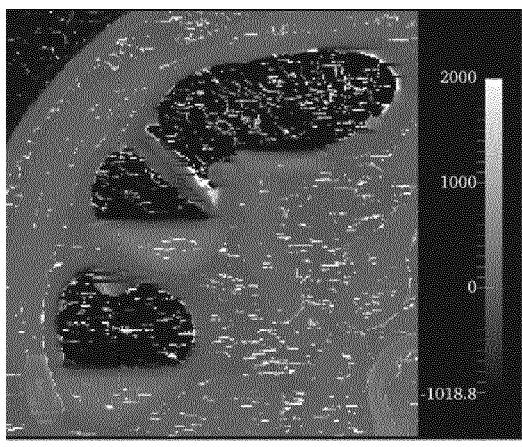
Figure 6:
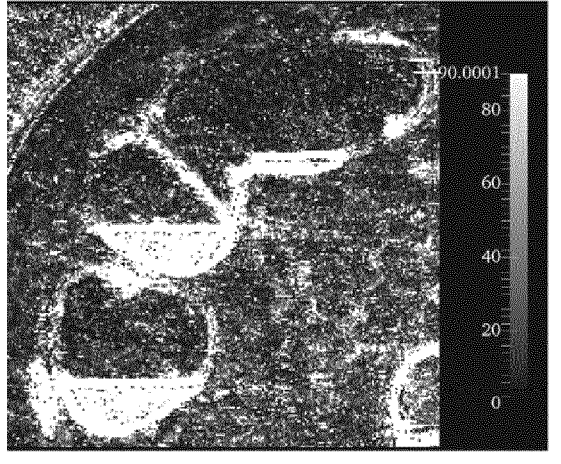
FIG. 6 represents an image representation of a model fit quality parameter derived for each voxel.
Figure 7:
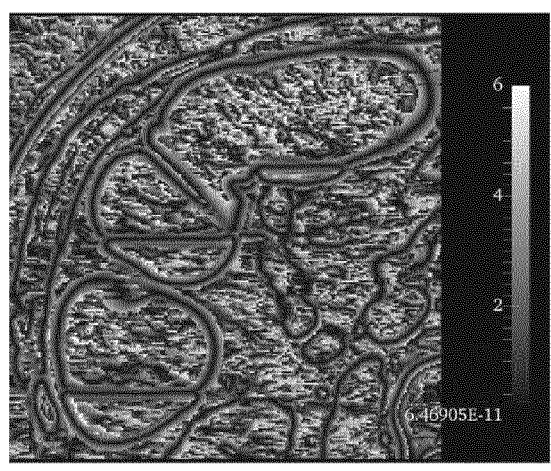
FIG. 7 represents an image representation of a determined absolute distance of each voxel from the material boundary of interest.

For example, FIG. 5(*a*) shows an image representing the values for the fitted model parameter $m_{low}$, for each voxel, and FIG. 5(*b*) shows an image representing the values for the parameter $m_{high}$. FIG. 6 shows an image representing the values for the quality fit parameter for each voxel. FIG. 7 shows an image representing the values for a secondary derived parameter of absolute distance of voxel i from the material transition boundary.

Based on the various derived parameters for each voxel i, masking of voxels is performed, based on further use of reference values or criteria for the parameter values. The masking may be based on derived images for the model parameters and fitting quality parameters in some examples. By way of example, the reference values may be pre-stored in a local or remote datastore. The reference values may be values known from prior scan data to be associated with voxels close to the material boundary of interest. By way of example, reference values may be used as threshold values, or decision criteria may include whether the voxel parameter values fall within a predefined tolerance range of the reference values.

A separate respective mask may be generated for each of at least a subset of the different fitting parameters and quality fit parameter.

In some examples, at least one mask may be generated based the quality fit parameter for each voxel, wherein each voxel is masked in dependence upon the quality fit parameter exceeding a pre-defined reference value or threshold for the quality fit.

Additionally or alternatively, at least one mask may be generated based on the values of $m_{high}$ and $m_{low}$ for each voxel, wherein each voxel is masked in dependence upon the derived values of $m_{high}$ and $m_{low}$ falling within a pre-defined tolerance range of a pre-determined pair of reference values for $m_{high}$ and $m_{low}$, the reference values corresponding to a particular material boundary of interest. Hence here, the masking is based on identifying a particular transition between two (or more) known materials, using prior knowledge of typical voxel values (e.g. Hounsfield values) within those two materials. By way of example, it is known that the Hounsfield values of air are around −1000, while the Hounsfield values of soft tissue are around 0. Voxels i belonging to the air-tissue transition in this case should thus fulfil the conditions $m_{high}(i) \approx 0$ and $m_{low}(i) \approx -1000$, and only voxels for which $m_{high}(i)$ and $m_{low}(i)$ fall within some predefined tolerance range of these prior values would be masked. By way of illustration, FIGS. 8-9 depict respective example masks for $m_{low}(i)$ and $m_{high}(i)$ for an air-tissue material transition.

Additionally or alternatively, at least one mask may be generated based on the distance, d, for each voxel, wherein each voxel is masked in dependence upon the derived distance value, d, falling within a pre-defined tolerance range of a reference value for d. Thus here, only voxels which lie within a pre-defined minimum proximity to the material boundary would be masked.

In accordance with one or more embodiments, a plurality of masks may be generated for different respective parameters and applied in combination to the volumetric image data. The resulting voxels located in mutually overlapping regions of the combination of masks are identified as candidate voxels.

Figure 8:
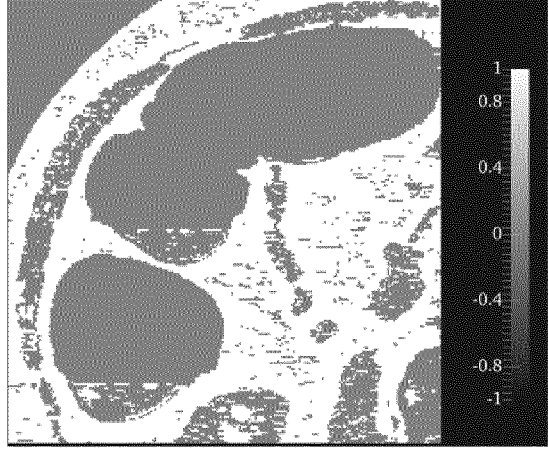
FIGS. 8-9 show masking of voxels based respectively on the $m_{low}$ and $m_{high}$ model parameter values determined for each voxel.
Figure 9:
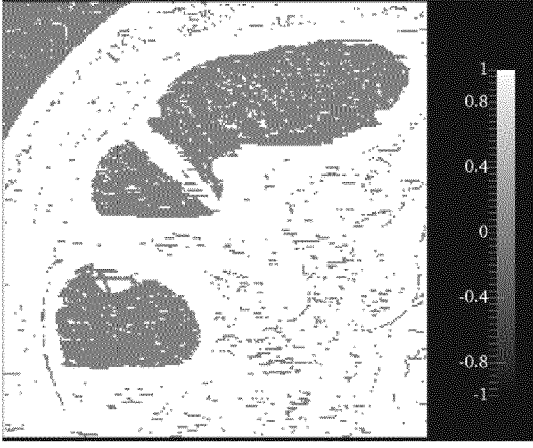
Figure 10:
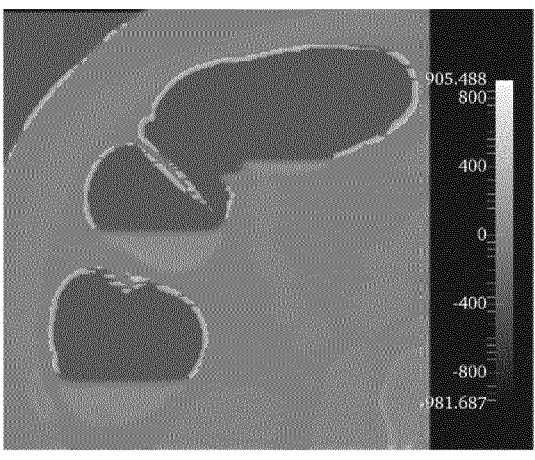
FIG. 10 shows the result of overlaying the masks of FIGS. 8 and 9 to the original volumetric image dataset.

One example is illustrated schematically in FIG. 10, which shows the result of overlaying the combination of the two masks shown in FIGS. 8-9. The resulting voxels in the overlapping regions between the masks are shown in white on FIG. 10, and it can be seen that these follow the wall of the colon depicted in the image data. The resulting voxels form a set of candidate voxels, meaning they are candidates for voxels which coincide most closely with the colon wall within the image data, or for which the model fit is best.

The deriving of the representation of the material boundary further comprises identifying from each of the candidate voxels a candidate point estimated to lie on the material boundary, based on the model-derived distance, d, of each voxel from the boundary, and based on a model-derived unit normal vector for the boundary.

In particular, the identifying of the candidate spatial point for each candidate voxel comprises identifying co-ordinates of a point a distance d from the voxel position along the boundary unit normal direction derived from the fitting parameters for the voxel.

In particular, for most cases, a flat plane is a good approximation of the shape of the boundary at a local region closest to a given voxel. Flat planes can be parameterized e.g. by the Hesse normal form, consisting of a unit vector $(n_x, n_y, n_z)$ and the distance d of the voxel to the boundary. Both of these parameters are fitting parameters of the model boundary transition function, and thus are pre-computed for each candidate voxel. A candidate spatial point for the material boundary can then be identified as the spatial point a distance d from the voxel along the direction of the boundary unit normal. Thus, for a voxel having co-ordinate position (i, j, k), the co-ordinate position, p, of a candidate point can be identified as $p=(i, j, k)+d*(n_x, n_y, n_z)$.

The resulting set of candidate spatial points derived for the full set of candidate voxels results in a list (or cloud) of points, all of them on the material boundary, but not necessarily coinciding with points on the voxel grid.

Figure 11:
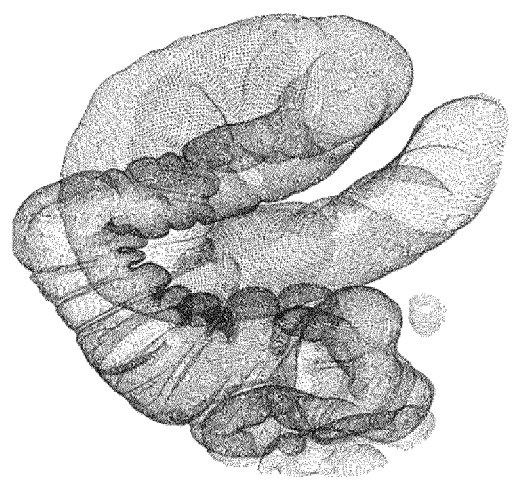
FIGS. 11-12 shows views of an extracted cloud of candidate points, the points of the cloud derived from the voxels which were situated in overlapping regions of the combination of applied masks.
Figure 11:
Figure 12:
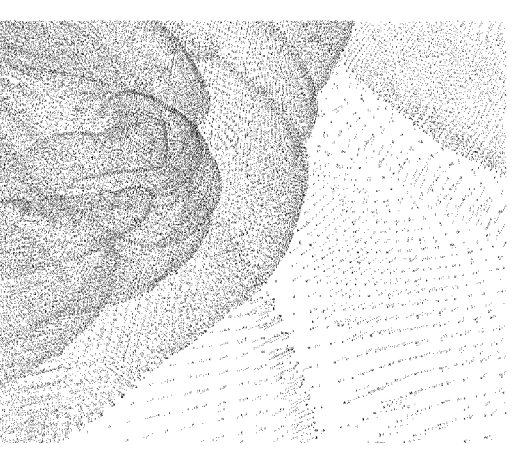

FIG. 11 shows an image representation of an example cloud of candidate points generated in this way. FIG. 12 shows a close, zoomed-in, view of the point cloud.

For each of the points in the point cloud, the unit normal vector n may be stored for later use. This may be useful for further rendering steps.

By way of example, according to one or more embodiments, a surface mesh representative of the material boundary may further be generated, the surface mesh containing the reduced subset of candidate points forming the cloud. The deriving the surface mesh may comprise linking points from the point cloud into triangles. These can be used for rendering.

Figure 13:
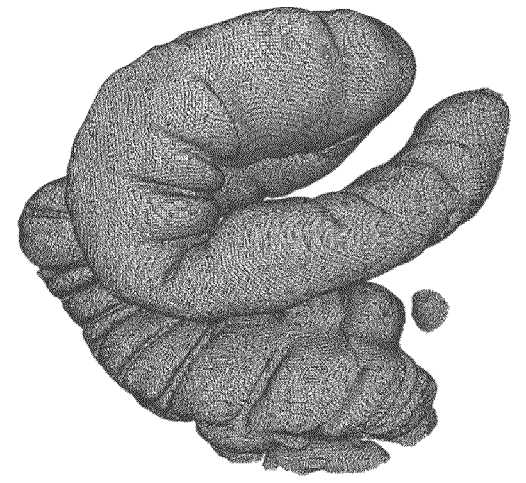
FIGS. 13-14 show views of an example surface mesh constructed based on candidate spatial points derived from the candidate voxels.
Figure 14:
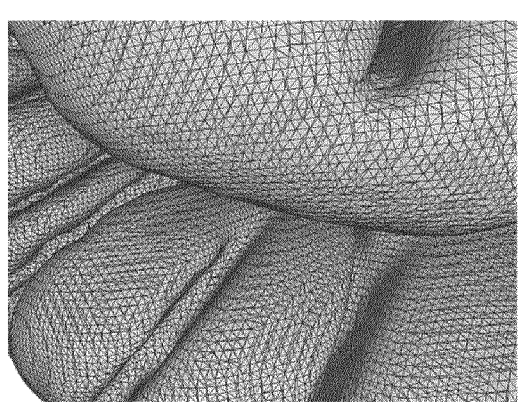
Figure 15:
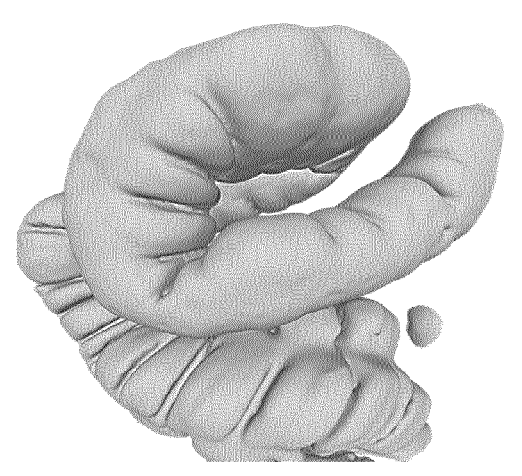
FIGS. 15-16 show views of a further example surface mesh.
Figure 16:
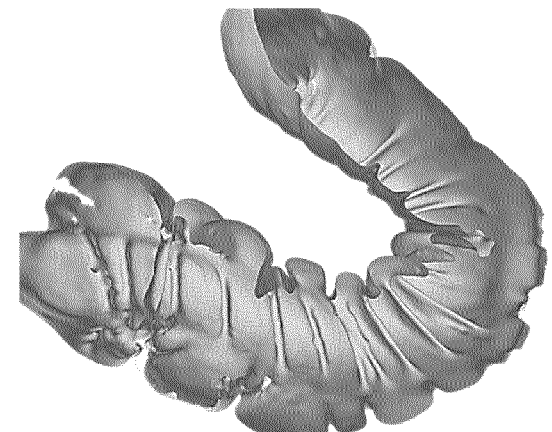

FIG. 13 shows an example surface mesh constructed based on the derived cloud of candidate points of FIG. 11. FIG. 14 shows a closer, zoomed, view of the surface mesh. FIGS. 16-18 show further example surface mesh renderings, wherein the triangles linking points have been filled, to provide a smooth surface representation of the wall of the colon. FIG. 16 shows a cut-away view into the interior lumen of the colon.

As mentioned above, in some examples, a new respective image may be generated representative of each of the fitting parameters, secondary parameters and the quality fit parameter, for each of the voxels. In some examples, some or all of these images may further be used to color the derived surface mesh, for the purpose of visualizing more information. The images may be rendered translucent and superimposed atop the mesh. A plurality of the images may be superimposed together on the mesh, with different colors, or a user interface may permit the user to selectively switch between different of the parameter images, superimposed on the mesh.

Although the above outlined example is described in relation to a two-material boundary, the same principles can be applied for more complex boundaries. One example is a multi-layered boundary. One example of this is a thin material layer (of material 2) embedded within another material region (material 1). In this case, the multi-layered boundary may simply be treated as a pair of two-material boundaries: a first boundary from material 1 to the thin layer of material 2, and then a second boundary from the layer of material 2 back to material 1. A single boundary transition function may be used which encompasses both two-material boundaries, or separate two-material transition functions may be applied successively to the volumetric image data to identify the pair of boundaries on either side of the thin layer.

In either case, the principles for estimating the pair of material boundaries using the boundary transition function are the same as those outlined above for the single two-material boundary.

A further example case is that of a three-material boundary (three material regions meeting at a common line). Here, again the same principles apply as for a two-material transition, except that the model of expected voxel values as a function of distance across the boundary (represented by the boundary transition function) has an additional directional dependency (direction of approach of the boundary), to account for the fact that there are three material regions meeting at a common boundary line. However, the boundary transition function still models voxel values as a function of position relative to the boundary. The model may additionally include model parameters (fitting parameters) related to an angle between the different material regions surrounding the boundary line, and/or an angle of the voxel relative to one or more of the different material regions, or relative to the boundary line. This then allows the boundary transition model to be fitted to the volumetric sub-region surrounding a given voxel regardless of its position within or relative to the different material regions.

As mentioned above, in accordance with one or more embodiments, the obtained volumetric image data may be spectral image data. The data may include a plurality of image data sets, each formed from data corresponding to a different spectral data channel, and wherein the method according to the invention is performed for each of the data sets, and wherein there is a different respective pre-determined material transition function for each spectral channel.

One example is use of x-ray spectral CT data. X-ray spectral CT is an imaging modality that extends the capabilities of a conventional x-ray CT system by acquiring projection data for a plurality of x-ray energies. This can be done by incorporating a detector which can discriminate between different x-Ray energies, e.g. an energy discriminating photon counting detector or energy integrating detector, or by sequentially changing the x-ray energy spectrum and sequentially acquiring corresponding detector data. Spectral x-ray data allows for discerning and quantifying materials comprised by the scanned object. This is because different materials may have different x-ray absorption spectra. An x-ray energy spectrum can be used which is known to be maximally or minimally absorbed by a material of interest for example.

Another example is use of MRI data. In multiparametric MRI, a similar principle can be applied, wherein two or more MR sequences can be cycled through, and a respective set of image data acquired for each. Different materials are represented with greater or lesser contrast for the different MR sequences (channels).

The example method workflow outlined above can be extended for application to spectral volumetric image data.

One example will now be outlined for spectral CT data. However, the same principles can also be applied for spectral image data derived from other modalities such as MRI or ultrasound.

Using spectral CT data, it is possible for example to create synthesized monoenergetic images at different keV (x-ray tube voltage) values. In these monoenergetic images, different materials show with different contrast.

With some minor modifications, the workflow described above can be adapted to handle data from two or more different spectral channels, which can allow for a more robust rendering of the material boundary.

The method comprises obtaining n different sets of spectral image data $I_i$, where n can be any integer number greater than 1, and wherein each image data set corresponds to image data acquired from a different respective spectral channel. A different spectral channel means that the projection data from which the respective image data set was reconstructed was obtained using a different respective x-ray tube voltage (or a different x-ray energy spectrum).

By way of one example, two image data sets $I_1$, $I_2$ may be received (n=2), each corresponding to a different x-ray energy channel (x-ray tube voltage), e.g. each corresponds to a different monoenergetic image data set. For example, $I_1$ at 45 keV (tube voltage) and $I_2$ at 125 keV.

A two-material transition may now be modelled by n different material boundary transition functions $g_i(m_{i,high}, m_{i,low}, d, n, \sigma)$ with i=1, . . . , n. The material parameters $m_{i,high}$ and $m_{i,low}$ are different for each of the spectral image data sets $I_i$, while the geometric parameters d, n, and $\sigma$ are the same for each dataset.

The fitting of the model function may be performed to optimize the matching of the model functions $g_i$ with all the spectral images $I_i$ simultaneously. In other words, the model functions are fitted to the respective spectral datasets simultaneously, and using a cost function which seeks to optimize the fitting of all models at the same time. For example, one may represent the spectral image data sets as a single dataset having a plurality of voxel values for each voxel. For example, if k is an index for the voxel and i=0, 1 is the index for the spectral image data set, and $I_{ik}$ is the voxel value for spectral image i at voxel k, then one may optimize e.g. the cost function $\Sigma_k (I_{0k}-g_{0k}(m_{0high}, m_{0low}, d, n, sigma))^2+(I_{1k}-g_{1k}(m_{1high}, m_{1low}, d, n, sigma))^2$.

From the fitting of each of the two model functions to each of the voxels of the respective spectral image dataset, estimations can be made for the respective model function fitting parameters for each voxel j. The fitting parameters include the material parameters $m_{i,high}(j)$ and $m_{i,low}(j)$ for each spectral image dataset $I_i$, (where $m_{i,low}$ is the minimum voxel value on one side of the material boundary, and $m_{i,high}$ is the maximum voxel value on the other side of the material boundary). The fitting parameters also include the geometric parameters d(j), n(j), $\sigma(j)$, which are the same for each of the image datasets $I_i$.

Further secondary parameters may additionally be derived for each spectral image dataset $I_i$, based on the derived fitting parameters. These include for example the absolute difference between $m_{i,high}(J)$ and $m_{i,low}(j)$.

Based on the fitting parameters, the secondary parameters, and a derived fit quality parameter for each voxel in each image dataset, candidate voxels may be determined. As described in the workflow above, this can be based on use of masking of voxels.

In particular, masking may be performed based on the determined model fitting parameters for each spectral dataset and based on one or more pre-determined reference values or reference criteria. The masking can be applied to image data of a single image dataset, but using masks derived based on the parameter values from a plurality of the spectral channels. In other words, the information obtained from multiple spectral channels can be used to identify the candidate voxels. For example, a first mask may be generated based on the fitting parameters from one spectral channel, and a second mask based on the fitting parameters from a second spectral channel, and based on pre-defined reference criteria for each, and wherein both masks are applied in combination to the image data of one of the two spectral channels, or a third spectral channel. Thus, information from multiple spectral channels can be taken into account, resulting in a much enhanced identification of the candidate voxels. The candidate voxels may be identified as those voxels located in regions of overlap between the two or more masks. This way, erroneous fitting results from one spectral channel may be more reliably discounted.

Once the candidate voxels have been identified, the remaining steps of the method are the same as those outlined in the previously described workflow for non-spectral data. In particular, candidate spatial points for the material boundary can be identified for each candidate voxel based on the model fitting parameters for the candidate voxel. This forms a cloud of candidate points for each. From these candidate points, a surface mesh may be constructed, for example by linking points into triangles.

Since the different spectral datasets can be used to identify boundaries between different pairs or sets of materials, the point cloud for each spectral dataset delimits a transition between different material pairs or sets. For example these may include one point cloud for an air to tissue transition, one for contrast medium to tissue, and one for air to contrast medium. By, for example, combining the point clouds for air to tissue and contrast medium to tissue, one consequently derives a composite point cloud for the overall tissue boundary. It is this which is sought for example in the case of seeking to identify a boundary of the colon wall. Thus, in this way, the process of virtual cleansing (discussed above) can be performed.

In accordance with any of the embodiments outlined above, the following variations may be applied.

In the examples, discussed above, it was assumed that the point spread function of the image scanning equipment used to acquire the image data was isotropic. However, in further examples, the point spread function of the scanner may be anisotropic. In this case, $\sigma$ may be replaced by a vector $\sigma$.

The point spread function of the scanner (isotropic or anisotropic) might be known a priori. In this case it does not need to be estimated and can be a fixed value in the algorithm.

In accordance with one or more embodiments, a preprocessing step may be applied in advance of the fitting of the model function to each voxel, the preprocessing for filtering the voxels to a reduced voxel set, based on identifying those voxels most likely to be close to the material boundary. Voxels which are estimated to have a low likelihood of being candidate voxels, close to the material boundary, may be discounted. The fitting of the model function may then be applied only to the voxels remaining after the filtering.

The filtering may be performed based on any of a number of different factors. One option includes selecting only those voxels whose voxel values lie within a pre-defined range of expected $m_{high}$ and $m_{low}$ values for either side of a material boundary being sought. Other options include detecting a representation of gradients of voxel values across the imaged volumetric region and selecting only those voxels lying in regions of relative high gradient.

Examples in accordance with a further aspect of the invention provide a processing arrangement which is adapted to perform a method in accordance with any example or embodiment outlined above or described below, or in accordance with any claim of this application.

The processing arrangement may in general comprise a single processor or a plurality of processors. It may be located in a single containing device, structure or unit, or it may be distributed between a plurality of different devices, structures or units. Reference therefore to the processing arrangement being adapted or configured to perform a particular step or task may correspond to that step or task being performed by any one or more of a plurality of processing components, either alone or in combination. The skilled person will understand how such a distributed processing arrangement can be implemented. The processing arrangement includes a communication module or input/output for receiving data and outputting data to further components.

The one or more processors of the processing arrangement can be implemented in numerous ways, with software and/or hardware, to perform the various functions required. A processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

A further aspect of the invention may provide a system comprising a processing arrangement as outlined above, and further comprising a display unit operatively coupled with the processing arrangement for use in displaying the generated representation of the material boundary within the image data. The processing arrangement may be adapted to generate a display control output for causing the display unit to display an image representation of the identified material boundary. The system may further include a user interface to permit a user to alter properties or settings of the performed method, and/or configure settings relating to the display of the material boundary on the display unit.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A computer-implemented method of processing volumetric image data for identifying a material boundary within the data, the method comprising:

obtaining volumetric image data representative of anatomical region of a subject;

for each of at least a subset of voxels in the anatomical region:

identifying a volumetric sub-region surrounding the voxel, the sub-region including at least a subset of directly neighboring voxels;

retrieving a pre-determined boundary transition function, the boundary transition function representing a model of expected voxel values as a function of distance across the material boundary to be identified;

fitting the pre-determined boundary transition function to the voxel values comprised within the volumetric sub-region, the fitting comprising determining fitting parameters of the model function;

determining a fit quality parameter indicative of a quality of the model function fit;

identifying candidate spatial points for the material boundary based on the determined fitting parameters and fit quality parameter for each voxel; and estimating the material boundary within the data based on at least a subset of the identified candidate points, wherein the boundary transition function models the voxel values as progressing from a minimum voxel value on one side of the material boundary to a maximum voxel value on the other side of the material boundary, and wherein the fitting parameters include at least one of:

the minimum voxel value ($m_{low}$);

the maximum voxel value ($m_{high}$);

a perpendicular distance of the voxel from the material boundary; and a unit normal vector of the material boundary.

2. The method as claimed in claim 1, wherein the identifying of the candidate spatial points comprises identifying candidate voxels, and wherein a respective candidate spatial point is identified for each candidate voxel based on the fitting parameters for the candidate voxel, the identifying of candidate voxels comprising performing masking of voxels in the imaged anatomical region based on one or more of the derived fitting parameter values and/or based on the derived quality parameter values.

3. The method as claimed in claim 2, wherein a separate respective mask is generated based on at least one of:

the quality fit parameter for each voxel, wherein each voxel is masked in dependence upon the quality fit parameter exceeding a pre-defined reference value for the quality fit;

the values of $m_{high}$ and $m_{low}$ for each voxel, wherein each voxel is masked in dependence upon the derived values of $m_{high}$ and $m_{low}$ falling within a pre-defined tolerance range of a pre-determined pair of reference values for $m_{high}$ and $m_{low}$, the reference values corresponding to a particular material boundary of interest;

the distance for each voxel, wherein each voxel is masked in dependence upon the derived distance value falling within a pre-defined tolerance range of a reference value.

4. The method as claimed in claim 2, wherein a plurality of masks are generated for different respective parameters and are applied in combination to the volumetric image data, and wherein the resulting voxels located in mutually over-lapping regions of the combination of masks are identified as the candidate voxels.

5. The method as claimed in claim 1, wherein
the fitting parameters include: the perpendicular distance of the voxel from the material boundary, and a unit normal vector of the material boundary; and
the identifying the candidate spatial points comprises identifying co-ordinates of a point a distance from the voxel position along the unit normal direction.

6. The method as claimed in claim 1, wherein the estimating the material boundary further comprises generating a surface mesh representative of the material boundary, the surface mesh containing at least a subset of the identified spatial points.

7. The method as claimed in claim 1, wherein the obtained volumetric image data comprises x-ray CT volumetric image data.

8. The method as claimed in claim 1, wherein the obtained volumetric image data comprises spectral image data, and includes a plurality of image data sets, each formed from data corresponding to a different spectral data channel, and wherein the method is performed for each of the data sets, and wherein there is a different respective pre-determined material boundary transition function for each spectral channel.

9. The method as claimed in claim 1, wherein the material boundary represents a structural wall of an anatomical structure.

10. The method as claimed in claim 9, wherein the material boundary represents the structural wall of an ana-tomical structure delimiting an interior lumen.

11. A device for processing volumetric image data for identifying a material boundary within the data, the device comprising:
a memory that stores a plurality of instructions; and
a processor coupled to the memory and configured to execute the plurality of instructions to:
obtain volumetric image data representative of ana-tomical region of a subject;

for each of at least a subset of voxels in the anatomical region:
identify a volumetric sub-region) surrounding the voxel, the sub-region including at least a subset of directly neighboring voxels,
retrieve a pre-determined boundary transition func-tion, the boundary transition function representing a model of expected voxel values as a function of distance across the material boundary to be iden-tified,
fit the pre-determined boundary transition function to the voxel values comprised within the volumet-ric sub-region, the fitting comprising determining fitting parameters of the model,
determine a fit quality parameter indicative of a quality of the model function fit;
identify candidate spatial points for the material bound-ary based on the determined fitting parameters and fit quality parameter for each voxel;
estimate the material boundary within the data based on at least a subset of the identified candidate spatial points, wherein the boundary transition function models the voxel values as progressing from a mini-mum voxel value on one side of the material bound-ary to a maximum voxel value on the other side of the material boundary, and wherein the fitting param-eters include at least one of:
the minimum voxel value;
the maximum voxel value;
a perpendicular distance of the voxel from the boundary; and
a unit normal vector of the boundary.

12. The device as claimed in claim 11, wherein the identifying of the candidate points comprises identifying candidate voxels, and wherein a respective candidate point is identified based on the fitting parameters for each candi-date voxel, the identifying of candidate voxels comprising performing masking of voxels in the imaged anatomical region based on one or more of the derived fitting parameter values and/or based on the derived quality parameter values.

* * * * *